US008844361B2

(12) United States Patent
Joyce

(10) Patent No.: US 8,844,361 B2
(45) Date of Patent: Sep. 30, 2014

(54) ULTRASONIC SENSOR CONTROL SYSTEM FOR OCCUPANCY SENSING

(75) Inventor: Jason Joyce, Carlsbad, CA (US)

(73) Assignee: The Watt Stopper, Inc., Carlsbad, CA (US)

( * ) Notice: Subject to any disclaimer, the term of this patent is extended or adjusted under 35 U.S.C. 154(b) by 295 days.

(21) Appl. No.: 13/191,673

(22) Filed: Jul. 27, 2011

(65) Prior Publication Data

US 2012/0024069 A1 Feb. 2, 2012

Related U.S. Application Data

(60) Provisional application No. 61/369,614, filed on Jul. 30, 2010.

(51) Int. Cl.
*G01N 29/00* (2006.01)
*G01S 15/04* (2006.01)
*H03K 17/94* (2006.01)
*G01S 7/52* (2006.01)

(52) U.S. Cl.
CPC ... *G01S 7/52004* (2013.01); *H03K 2217/94005* (2013.01); *G01S 15/04* (2013.01); *H03K 17/94* (2013.01)
USPC .............................................. 73/632; 73/649

(58) Field of Classification Search
USPC ..................................... 73/632, 649; 340/541
See application file for complete search history.

(56) References Cited

U.S. PATENT DOCUMENTS

| | | | | |
|---|---|---|---|---|
| 4,873,469 A | * | 10/1989 | Young et al. | 315/155 |
| 5,361,070 A | * | 11/1994 | McEwan | 342/21 |
| 5,640,143 A | * | 6/1997 | Myron et al. | 340/541 |
| 5,986,357 A | * | 11/1999 | Myron et al. | 307/116 |
| 6,026,340 A | * | 2/2000 | Corrado et al. | 701/47 |
| 6,272,411 B1 | * | 8/2001 | Corrado et al. | 701/45 |
| 6,285,912 B1 | * | 9/2001 | Ellison et al. | 700/11 |
| 6,798,341 B1 | * | 9/2004 | Eckel et al. | 340/521 |
| 7,411,489 B1 | * | 8/2008 | Elwell et al. | 340/501 |
| 7,432,690 B2 | * | 10/2008 | Williams et al. | 323/266 |
| 7,800,049 B2 | * | 9/2010 | Bandringa et al. | 250/239 |
| 7,962,285 B2 | * | 6/2011 | Breed | 701/472 |
| 8,025,118 B2 | * | 9/2011 | Scheucher | 180/68.5 |
| 8,610,307 B2 | * | 12/2013 | Zerbe et al. | 307/43 |

OTHER PUBLICATIONS

Airforce Research Laboratory, Solid state Grid modulator Mar. 2001.*

* cited by examiner

*Primary Examiner* — J M Saint Surin
(74) *Attorney, Agent, or Firm* — K. David Crockett, Esq.; Paul J. Backofen, Esq.; Crockett & Crockett, PC

(57) ABSTRACT

An active ultrasonic room occupancy sensor with the output amplitude of the transmitter controlled by the amplitude of power applied to the transmitter to control the zone of coverage for a sensor. An adjustable voltage regulator under control of a microcontroller applies controlled amplitude voltage to the transmitter to adjust the output amplitude of the transmitter. The adjustable amplitude transmitter allows an occupancy sensor to have its total output energy adjusted to conform to the area to be covered. Lowering the total ultrasonic energy in the monitored space lowers the sensitivity of the receiver to inappropriate activations. Lowering the input power to the transmitter also lowers the total internal system noise and provides an improved signal to noise ratio in the receiver. Alternatively, the power applied to the receiver may also be controlled by an adjustable voltage regulator under control of the microcontroller to improve receiver efficiency.

12 Claims, 3 Drawing Sheets

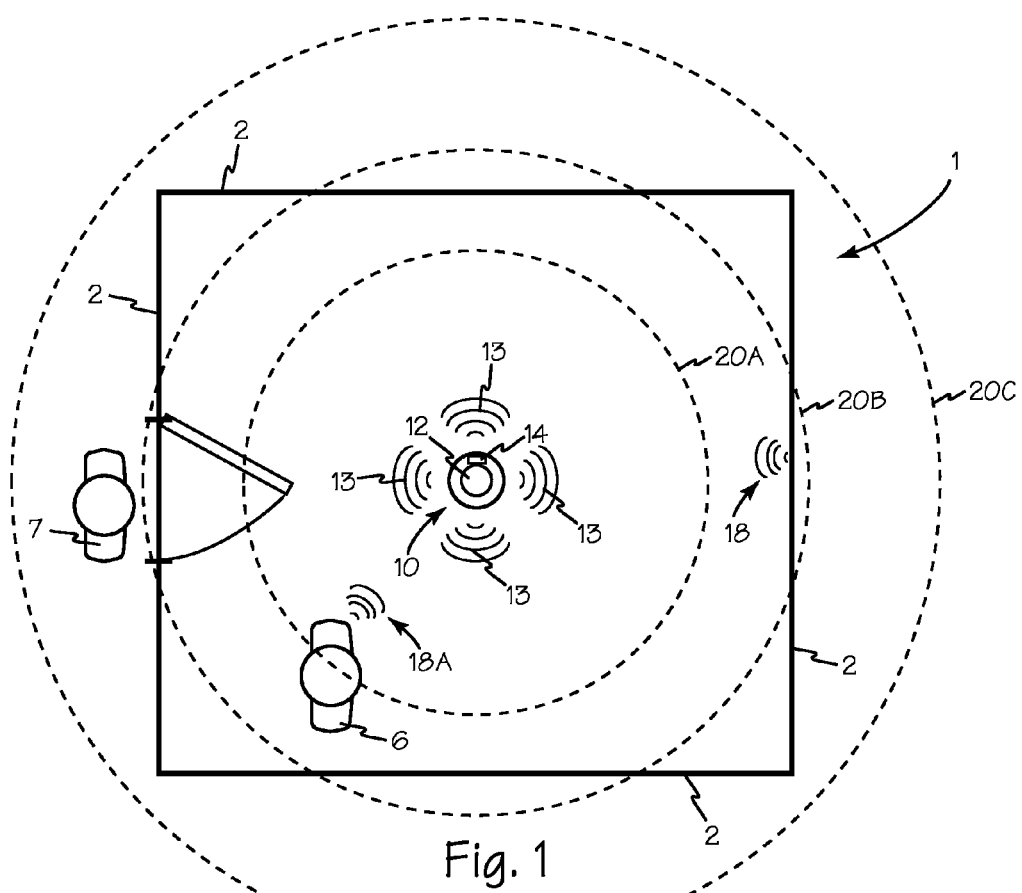
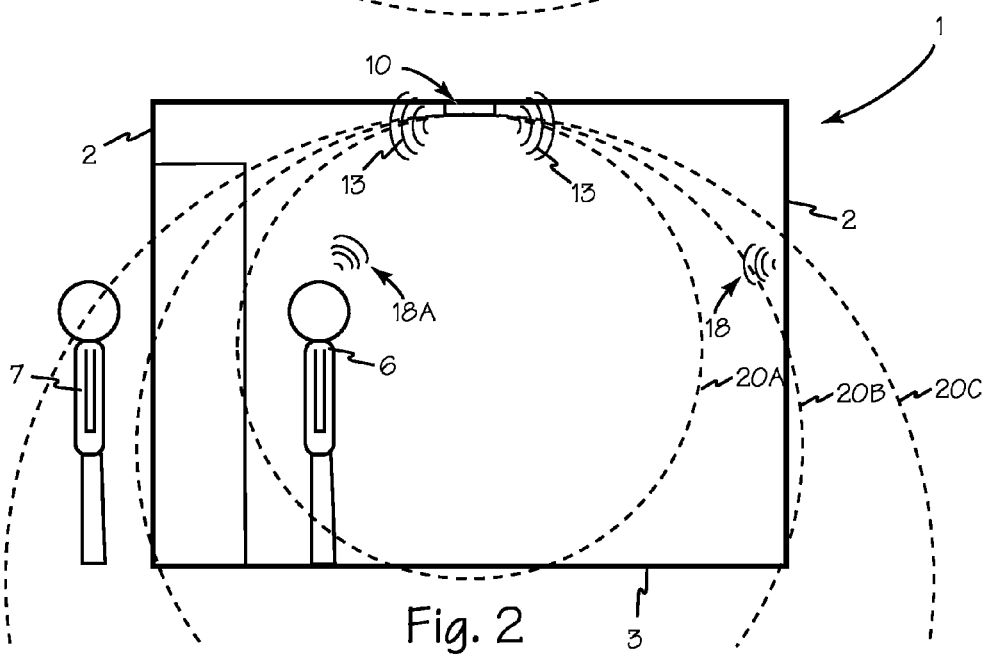

ULTRASONIC SENSOR CONTROL SYSTEM FOR OCCUPANCY SENSING

RELATED APPLICATIONS

This application claims priority to U.S. Provisional Patent Application 61/369,614 filed Jul. 30, 2010.

FIELD OF THE INVENTIONS

The inventions described below relate the field of electrical controls and more specifically, sensors for automatically controlling electrical loads such as lighting.

BACKGROUND OF THE INVENTIONS

Active ultrasonic room occupancy sensors are equipped with an ultrasonic transmitter having an output with a fixed amplitude. The size of the zone of coverage was adjusted by selection of the transmitter plate which was mechanically connected to the output crystal. This configuration often resulted in sensors with too large a coverage area being selected for a given area. With fixed energy transmitters, distant targets reflect significant energy leading to inappropriate activations. The sensitivity of the receiver is often ineffective in minimizing inappropriate activations.

SUMMARY

The devices and methods described below provide for an active ultrasonic room occupancy sensor with the output amplitude of the transmitter controlled by the amplitude of power applied to the transmitter to control the zone of coverage for a sensor. An adjustable voltage regulator under control of a microcontroller applies controlled amplitude voltage in the range of 5 to 9 VDC to the transmitter to adjust the output amplitude of the transmitter. The adjustable amplitude transmitter allows an occupancy sensor to have its total output energy adjusted to conform to the area to be covered. Lowering the total ultrasonic energy in the monitored space lowers the sensitivity of the receiver to inappropriate activations. Lowering the input power to the transmitter also lowers the total internal system noise and provides an improved signal to noise ratio in the receiver.

An active ultrasonic room occupancy sensor may also control of the amplitude of power applied to the receiver to control the sensitivity of the receiver. An adjustable voltage regulator under control of a microcontroller applies controlled amplitude voltage in the range of 5 to 9 VDC to the receiver to adjust the output amplitude of the receiver. Lowering the level of power applied to the input of an ultrasonic receiver also lowers the input noise level to the receiver. In multistage receiver systems the power is controlled to the first stage where the input signal is relatively small and the signal to noise ratio is relatively high. Improving the performance of the first stage provides correspondingly larger benefits in subsequent stages where both the system noise and the sensor signal are both amplified.

An active ultrasonic room occupancy sensor may control the power applied to both the transmitter and the receiver simultaneously. A single 24 VDC power supply may apply output power to an adjustable voltage regulator under control of the microcontroller which reduces the power applied to both the transmitter and the receiver to about 5 to 9 VDC. Control of the adjustable voltage regulator may be accomplished open loop or closed loop.

An active ultrasonic room occupancy sensor with an improved power system includes an intermediate power regulator between the 24 VDC power supply and the adjustable voltage regulator. The fixed regulator steps down the applied power from 24 VDC to about 12 VDC and the adjustable regulator reduces the power to 5 to 9 VDC as discussed above. The fixed regulator is a high efficiency switching regulator that performs two functions. First, it lower the noise from the main 24 VDC power supply and lower noise in the system improves the receiver efficiency. Second, the fixed regulator reduces total power consumption and wasted heat since each regulator is only regulating down a few volts from the input power applied. Use of a high efficiency fixed regulator to apply power to the adjustable regulator also eliminates the need for a feedback loop to monitor the output of the power supply.

BRIEF DESCRIPTION OF THE DRAWINGS

FIG. 1 is a top view of a room equipped with an adjustable amplitude active ultrasonic occupancy sensor.

FIG. 2 is a side view of the room of FIG. 1.

DETAILED DESCRIPTION OF THE INVENTIONS

Figure 3:
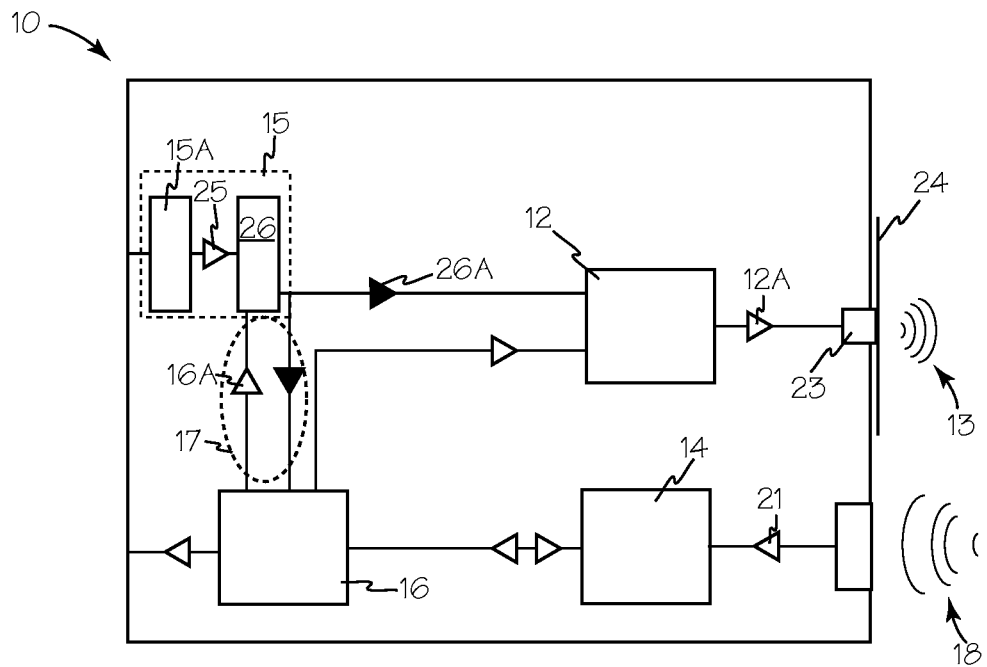
FIG. 3 is a block diagram of adjustable amplitude active ultrasonic occupancy sensor.

FIG. 1 is a top view, and FIG. 2 is a side view of room 1 equipped with adjustable amplitude active ultrasonic occupancy sensor 10 which is illustrated in FIG. 3. Sensor 10 includes a transmitter 12 and a receiver 14 which receives energy from power supply 15. Operation of transmitter 12, receiver 14 and power supply 15 are all controlled by microprocessor or controller 16. Transmitter 12 continuously transmits ultrasonic energy 13 into room 1. Ultrasonic energy 13 is reflected as incoming energy 18 by anything occupying room 1 including walls 2 and floor 3. The amplitude of power applied to transmitter 12 can be adjusted to control the amplitude of ultrasonic output signal 13 and thus, the amplitude of reflected signals from the contents of the room, such as reflected signal 18. The amplitude of output energy 16 is set such that reflected signals 18 from the edges of a desired zone of sensitivity such as zones 20A, 20B and 20C are at or below the noise threshold of receiver 19.

Similarly, the amplitude of the power applied to receiver 19 can be adjusted to control the sensitivity of the receiver. Controlling the amplitude of the power applied to the receiver lowers the noise input to the receiver improving the receiver's efficiency. With this configuration, a measurable disturbance of reflected energy 18 will result in a change in measurable signal 21 at receiver 19 thus permitting the amplitude of power applied to receiver 19 to control the level of movement or activity detected within the sensitivity zone, such as zone 20B, that triggers sensor 10.

Referring now to FIG. 3, in operation, transmitter 12 operates as an ultrasonic oscillator under control of controller 16. Output signal 12A is conveyed to transmitter crystal 23 which is mechanically connected to output plate 24. The vibrations of crystal 23 cause output plate 24 to create transmitter signals such as ultrasound energy 16 which is transmitted to the space to be monitored such as room 1. Input or system power 25 to adjustable regulator 26 is about 24 VDC with output power 26A of regulator 26 generally in the range of 5-9 VDC. Output power 26A may also be applied to controller 16 to create feedback loop 17 to enable accurate control of the power applied to the transmitter while main power supply 15A may be an inexpensive, loosely regulate supply.

In a room such as room 1 equipped with adjustable amplitude active ultrasonic occupancy sensor 10, the amplitude of transmitter 12 can be adjusted such that the amplitude of signals 18A reflected by room occupant 6 are measurable and little or no ultrasonic energy is reflected from anyone or anything, such as non-occupant 7, outside the established sensitivity zone such as sensitivity zone 20B.

Figure 4:
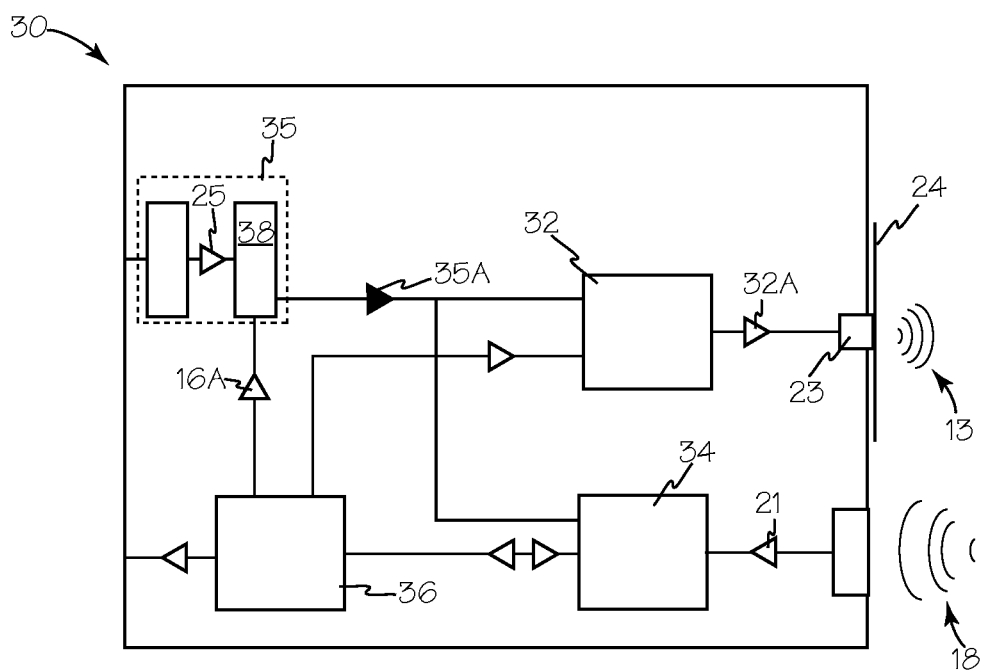
FIG. 4 is a block diagram of an active ultrasonic occupancy sensor with power adjustable transmitter and receiver.

Referring now to FIG. 4, ultrasonic occupancy sensor 30 includes a transmitter 32 and a receiver 34 which receives energy from power supply 35 and operates open loop, without a feedback loop such as feedback loop 17 of FIG. 3. Operation of transmitter 32, receiver 34 and power supply 35 are all controlled by microprocessor or controller 36. Power supply 35 includes adjustable voltage regulator 38 under control of controller 36. The amplitude of power 35A applied to transmitter 32 can be adjusted to by the controller to control the amplitude of ultrasonic output signal 13 and thus, the amplitude of reflected signals from the contents of the room, such as reflected signal 18. Adjustable power 35A may also be applied to receiver 34 can be adjusted to control the sensitivity of the receiver.

Figure 5:
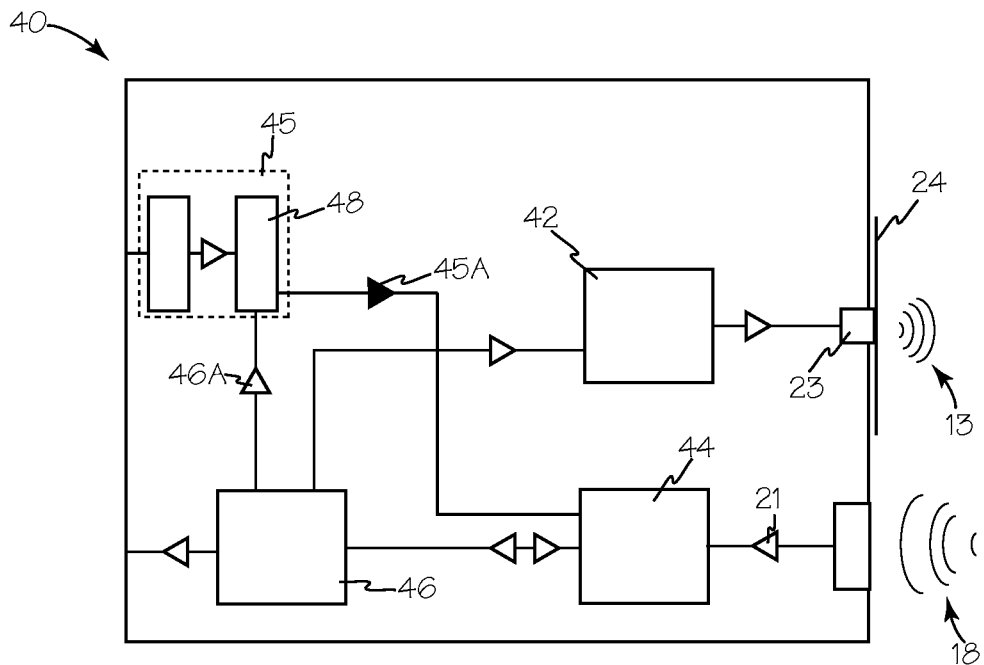
FIG. 5 is a block diagram of an active ultrasonic occupancy sensor with a power adjustable receiver.

Referring now to FIG. 5, ultrasonic occupancy sensor 40 includes a transmitter 42 and a receiver 44 which receives energy from power supply 45. Operation of transmitter 42, receiver 44 and power supply 45 are all controlled by microprocessor or controller 46. Power supply 45 includes adjustable voltage regulator 48 under control of controller 36. The amplitude of power 45A applied to receiver 44 can be adjusted to by the controller to control the noise and the sensitivity of the receiver.

Figure 6:
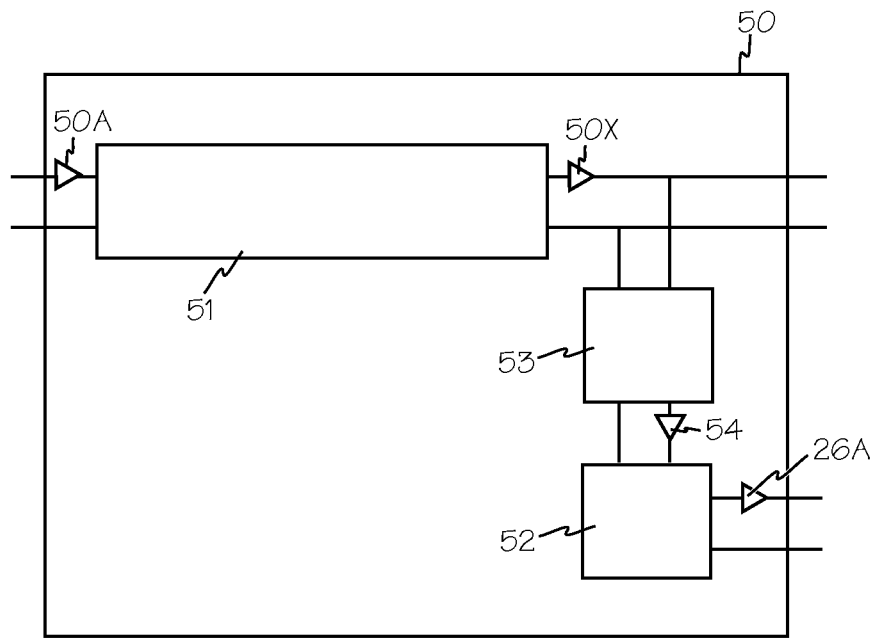
FIG. 6 is a block diagram of a power supply for an active ultrasonic occupancy sensor.

Referring now to FIG. 6, power supply 50 may be used with active ultrasonic occupancy sensors 10, 30 or 40. Power supply 50 includes main power supply 51 which processes input power 50A and produces output power 50X. Power supply 50 includes adjustable voltage regulator 52 which may be controlled by any sensor microcontroller such as controller 16 to produce output power 26A. Power supply 50 also includes fixed voltage regulator 53 which receives output power 50X, transforms it into intermediate power 54, and applies intermediate power 54 to adjustable voltage regulator 52. Intermediate power 54 may have any suitable voltage between the voltage of output power 50X and the voltage of output power 26A. Output power 50X is generally about 24 VDC, intermediate power 54 is generally about 12 VDC and output power 26A is generally in the range of 5-9 VDC. Other suitable voltages and voltage ranges may also be used.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. An active ultrasonic occupancy sensor comprising:
    an ultrasonic transmitter;
    an ultrasonic receiver;
    a power supply applying power to an adjustable voltage regulator which applies adjustable amplitude power to the ultrasonic transmitter;
    a microcontroller controlling the ultrasonic transmitter and the ultrasonic receiver by controlling the amplitude of the output voltage of the adjustable regulator.

2. The active ultrasonic occupancy sensor of claim 1 wherein the power from the power supply has a voltage of about 24VDC and the adjustable voltage regulator provides adjustable power with a voltage in the range of 5-9VDC.

3. The active ultrasonic occupancy sensor of claim 1 further comprising:
    a fixed voltage regulator which receives power from the power supply and applies power to the adjustable voltage regulator.

4. The active ultrasonic occupancy sensor of claim 3 wherein the fixed voltage regulator applies power to the adjustable voltage regulator with a voltage of 12VDC.

5. An active ultrasonic occupancy sensor comprising:
    an ultrasonic transmitter;
    an ultrasonic receiver;
    a power supply applying power to an adjustable voltage regulator which applies adjustable amplitude power to the ultrasonic receiver;
    a microcontroller controlling the ultrasonic transmitter and the ultrasonic receiver by controlling the amplitude of the output voltage of the adjustable regulator.

6. The active ultrasonic occupancy sensor of claim 5 wherein the power from the power supply has a voltage of about 24VDC and the adjustable voltage regulator provides adjustable power with a voltage in the range of 5-9VDC.

7. The active ultrasonic occupancy sensor of claim 5 further comprising:
    a fixed voltage regulator which receives power from the power supply and applies power to the adjustable voltage regulator.

8. The active ultrasonic occupancy sensor of claim 7 wherein the fixed voltage regulator applies power to the adjustable voltage regulator with a voltage of 12VDC.

9. An active ultrasonic occupancy sensor comprising:
    an ultrasonic transmitter;
    an ultrasonic receiver;
    a power supply applying power to an adjustable voltage regulator which applies adjustable amplitude power to the ultrasonic transmitter and the ultrasonic receiver;
    a microcontroller controlling the range of the ultrasonic transmitter and the sensitivity of the ultrasonic receiver by controlling the amplitude of the output voltage of the adjustable regulator.

10. The active ultrasonic occupancy sensor of claim 9 wherein the power from the power supply has a voltage of about 24VDC and the adjustable voltage regulator provides adjustable power with a voltage in the range of 5-9VDC.

11. The active ultrasonic occupancy sensor of claim 9 further comprising:
    a fixed voltage regulator which receives power from the power supply and applies power to the adjustable voltage regulator.

12. The active ultrasonic occupancy sensor of claim 11 wherein the fixed voltage regulator applies power to the adjustable voltage regulator with a voltage of 12VDC.

* * * * *